United States Patent [19]

Arnold et al.

[11] Patent Number: 4,774,960

[45] Date of Patent: Oct. 4, 1988

[54] METHOD AND APPARATUS FOR MEASURING BLOOD PRESSURE

[75] Inventors: Jeff Arnold, Ridgewood; Neil Judell, Plainfield; Michael Zelin, Plainsboro, all of N.J.

[73] Assignee: Datascope Corporation, Paramus, N.J.

[21] Appl. No.: 925,366

[22] Filed: Oct. 30, 1986

[51] Int. Cl.$^4$ ............................................. A61B 5/02
[52] U.S. Cl. .................................... 128/681; 128/682; 128/677
[58] Field of Search .................. 128/672, 677–686

[56] References Cited

U.S. PATENT DOCUMENTS

| 4,262,675 | 4/1981 | Kubo et al. | 128/680 |
| 4,263,918 | 4/1981 | Swearingen et al. | 128/681 |
| 4,484,584 | 11/1984 | Uemura | 128/680 |
| 4,543,962 | 10/1985 | Medero et al. | 128/680 X |
| 4,651,747 | 3/1987 | Link | 128/677 |

Primary Examiner—Kyle L. Howell
Assistant Examiner—Angela D. Sykes
Attorney, Agent, or Firm—Darby & Darby

[57] ABSTRACT

A method and apparatus are disclosed for tracking instantaneous changes in blood pressure. The invention is utilized in an oscillometric blood pressure measuring apparatus of the type measuring pulsatile perturbations in a patient's blood pressure at a plurality of different measurement pressures of a sphygmomanometer cuff, to derive a blood pressure model for the patient, the model being stored in the apparatus as a series of pulsatile perturbations and the associated cuff pressures. A characteristic curve is generated so as to approximate the stored model in the vicinity of a predefined index value of cuff pressure. The pressure of the cuff is maintained within a predetermined range, r, of the index value, while changes in the index value are tracked by sensing a pulsatile perturbation in the cuff pressure, deriving the corresponding value for cuff pressure from the characteristic curve, and utilizing the derived pressure as a new estimate for the index value. In a preferred embodiment, the characteristic curve is realized as an equation defining a straight line.

36 Claims, 5 Drawing Sheets

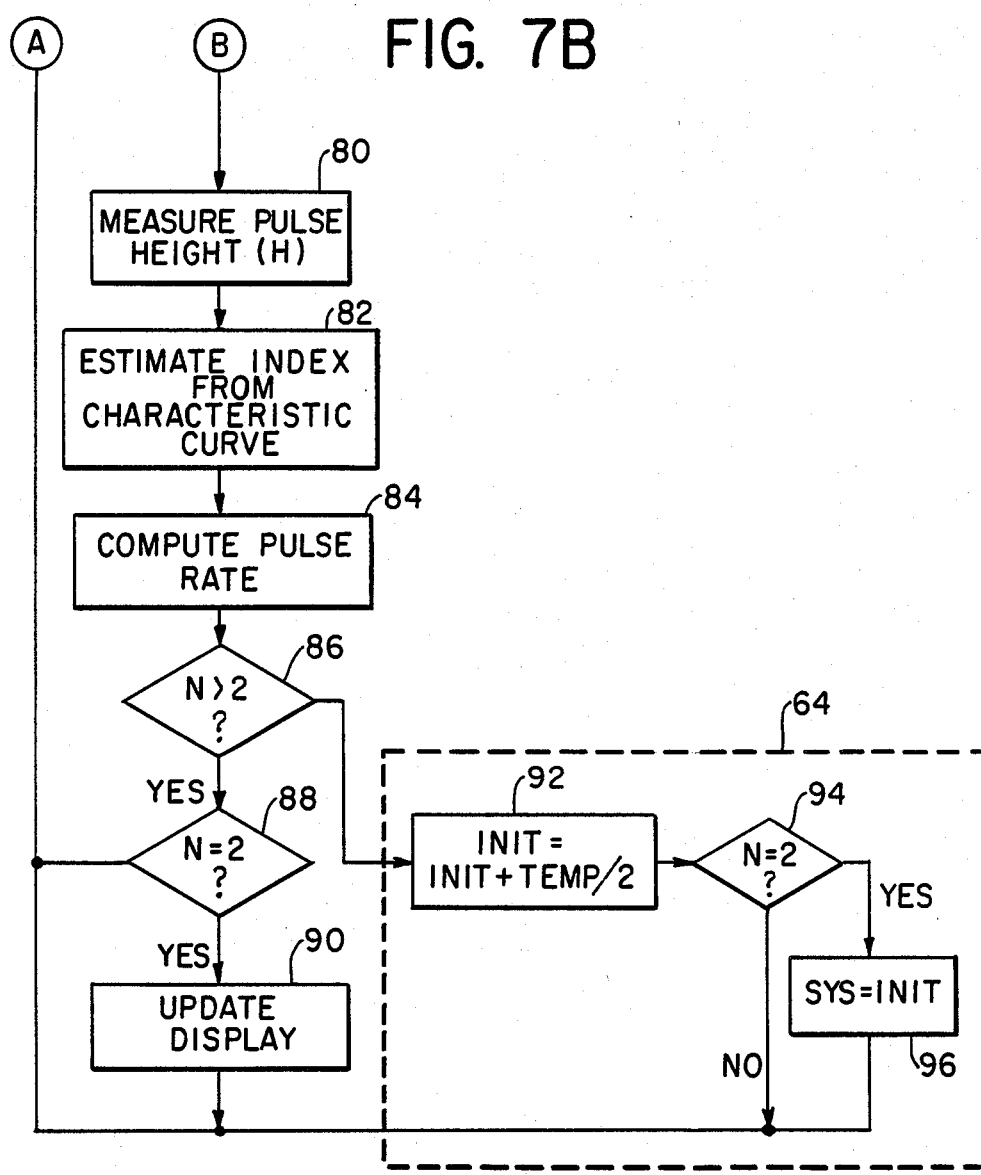

METHOD AND APPARATUS FOR MEASURING BLOOD PRESSURE

FIELD OF THE INVENTION

The present invention relates generally to the measurement of blood pressure and, more particularly, concerns a method and apparatus for measuring blood pressure automatically, which method and apparatus permit rapid sensing of changes in blood pressure.

BACKGROUND OF THE INVENTION

Blood pressure in the human arterial system varies, with the heartbeat, between a maximum or "systolic" value and a minimum or "diastolic" value. Perhaps, the most familiar device for measuring blood pressure is an inflatable cuff or "sphygmomanometer". When the sphygomomanometer is inflated to a pressure between the diastolic and systolic values, the section of artery beneath the cuff collapses and opens with blood pressure variations during the cardiac cycle, collapsing when arterial pressure drops below the cuff pressure and reopening as the arterial pressure increases above the cuff pressure. Should the sphygomanometer be inflated to a pressure which is not between diastolic and systolic, collapse and reopening of the artery does not occur. A meaningful characterization of a patient's blood pressure can therefore be obtained by varying cuff pressure through a range or continuum of values and noting the onset and cessation of arterial activity. The cuff pressure at which arterial activity sets in would then be designated as the diastolic value, and the cuff pressure at which arterial activity ceases would be designated as the systolic value.

Collapse and reopening of an artery produces characteristic "Korotkoff" sounds which can be detected through a stethoscope, ultrasound transducer, or similar device. A familiar procedure for measuring blood pressure has therefore involved sensing the range of cuff pressures over which the Korotkoff sounds can be detected. This procedure requires a skillful operator when performed manually and, when automated, is prone to errors.

Another phenomenon produced by the collapse and reopening of a constricted artery is the production of a pulsatile perturbation in the cuff pressure with each collapse and reopening of the artery. Methods making use of this phenomenon are referred to as "oscillometric". By applying a sequence or continuum of pressures to the cuff and measuring the accompanying pulsatile perturbations, it is possible to obtain a graph of pulse height (or other pulse characteristics, such as a time derivative) versus cuff pressure, which models the patient's blood pressure. Known systems have utilized various techniques for accurate measurement of pulse characteristics (or heights) and storage of the resultant curve which models the patient's blood pressure. For example, U.S. Pat. No. 4,263,918 discloses such a system which measures pulse heights, converts them to digital form and makes use of a microcomputer for processing and storage.

Experiments indicate that the curve which models a patient's blood pressure has a predictable relationship between the pulse heights occurring at various cuff pressures and that this relationship remains consistent over a large population and a variety of absolute arterial pressures. Specifically, the maximum pulsatile perturbation is found to occur at approximately the mean (time-averaged) value of arterial pressure. Moreover, at systolic pressure the perturbation is normally half of that at mean pressure, and at diastolic pressure, the perturbation is approximately 70% of that at mean pressure. These relationships have been found to be substantially stable over time and relatively independent of absolute pressure.

In certain environments, for example, in an operating room, it is necessary to monitor a patient's blood pressure on a constant basis, in order to assure a rapid response to sudden blood pressure changes that might endanger the patient's life or health. In this regard, known oscillometric methods and apparatus for measuring blood pressure have been entirely inadequate. One of the primary reasons for this has been that oscillometric devices require the re-derivation of the full model each time a measurement is provided. This can typically take a minute or longer. During this time the patient could be experiencing a life threatening trauma, and this fact might not be known until the model derivation was complete and a dangerous blood pressure condition indicated.

Broadly, it is an object of the present invention to overcome shortcomings of known oscillometric methods and apparatus for measuring blood pressure which result from the relatively long time required to derive a model of the patient's blood pressure. It is specifically an object of the present invention to achieve a substantial improvement in the speed of detection of changes in the blood pressure of a patient, to the point where a typical detection could be accomplished in about two seconds.

It is yet another object of the present invention to provide a method and apparatus which are readily adaptable to existing automatic blood pressure measuring equipment to achieve a substantial improvement in the speed of detection of changes in blood pressure. It is specifically contemplated that apparatus in accordance with the present invention be capable of being readily retrofitted into existing automatic blood pressure measuring equipment.

It is also an object of the present invention to provide a method and apparatus for rapid measurement of blood pressure which are reliable and convenient in use, yet relatively simple and inexpensive.

In accordance with the present invention, instantaneous changes in a patient's blood pressure are accurately tracked. A characteristic curve is generated so as to approximate the stored blood pressure model in the vicinity of a predefined index value of cuff pressure. The pressure of the cuff is maintained within a predetermined range, r, of said index value, while tracking changes in the index value by sensing a pulsatile perturbation in the cuff pressure, deriving the corresponding value for cuff pressure from the characteristic curve, and utilizing the derived pressure as a new estimate for the index value.

BRIEF DESCRIPTION OF THE DRAWING

The foregoing brief description, as well as further objects, features and advantages of the present invention will be more completely understood from the following detailed description of a presently preferred, but nonetheless illustrative embodiment, with reference being had to the drawing, in which:

FIGS. 7A and 7B, when joined at the connections A and B, provide a flow chart demonstrating the operation of index characteristic estimator 60 of FIG. 5; and FIG. 8 illustrates the steps comprising the operation in block 82 of FIG. 7B, for the preferred embodiment of the invention.

DETAILED DESCRIPTION OF THE PREFERRED EMBODIMENT

Figure 1:
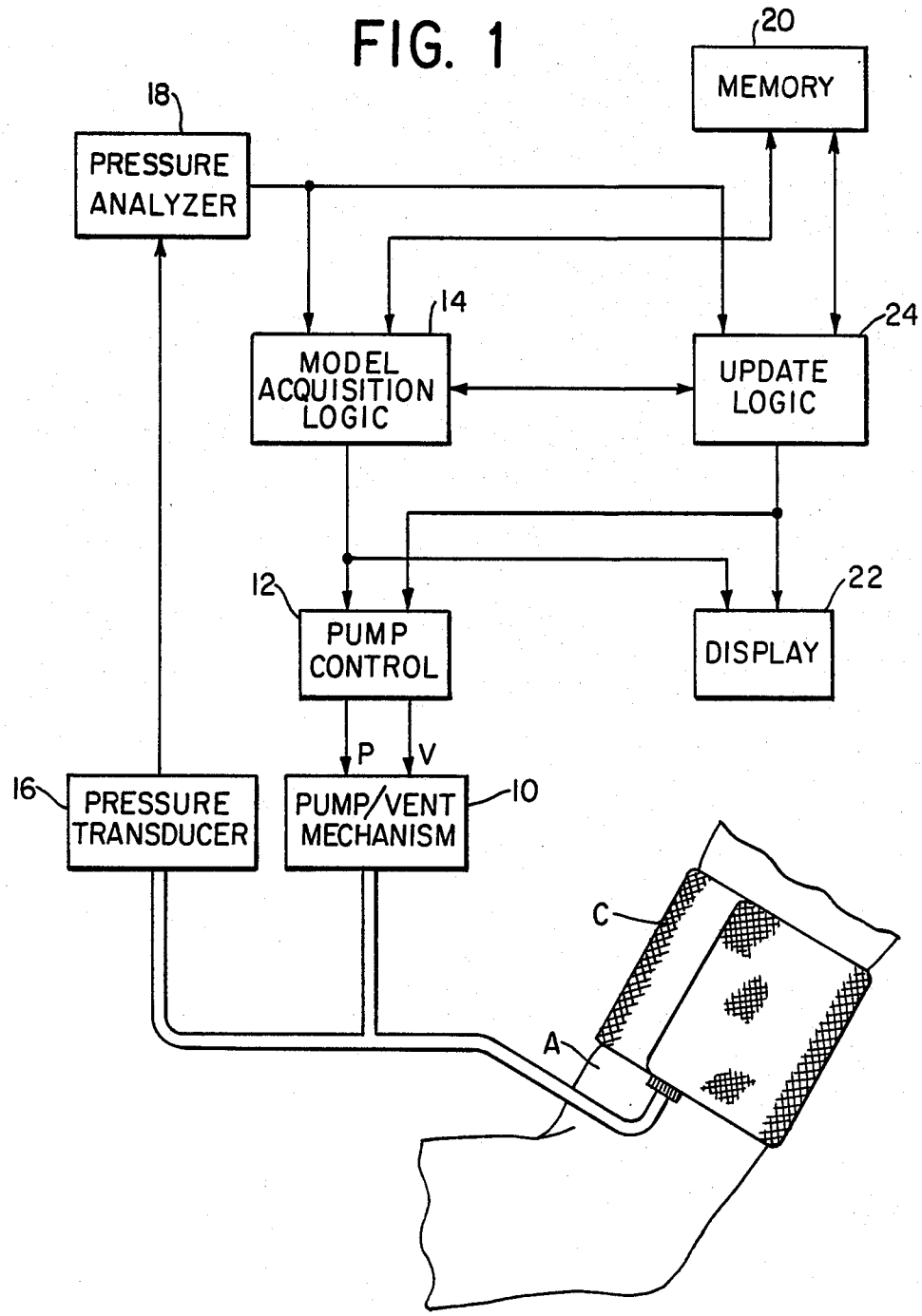
FIG. 1 is a functional block diagram illustrating a blood pressure measurement system incorporating objects and features of the present invention.

Referring now to FIG. 1, there is illustrated a functional block diagram of an automatic blood pressure measuring system incorporating objects and features of the present invention. A conventional sphygmomanometer cuff C is wrapped about, for example, a patient's arm. The pressure applied to cuff C is determined by operating a conventional pump/vent mechanism 10, by means of a pump control 12, which applies either a pump signal (P) or a vent signal (V) to pump/mechanism 10. The operation of pump control 12 is, in turn, controlled by model acquisition logic 14, which is programmed to produce a predetermined sequence of nominal pressures within cuff C.

The actual instantaneous pressure in cuff C is sensed by a conventional pressure transducer 16, which produces an electrical signal representative of the sensed pressure, which signal is applied to pressure analyzer 18. This pressure analyzer extracts signals representing the pulsatile pressure perturbations due to the patient's heart beat and provides two fundamental signals to model acquisition logic 14: (i) information relating to the pulsatile perturbation; and (ii) the accompanying cuff pressure. Various information about the pulsatile perturbations has been utilized to generate blood pressure characteristics. This includes various derivatives of wave forms representing the actual pulses and the amplitude of the pulses. However, the pulse amplitude is the most commonly used characteristic.

In model acquisition logic 14, the pulsatile information and cuff pressure are converted to a processable form (e.g. digital information) and are then stored in a conventional memory 20. Model acquisition logic also operates a conventional display 22 which may indicate such parameters as systolic pressure, diastolic pressure, mean pressure, and pulse rate (derived in model acquisition logic 14).

Thus far, the block diagram of FIG. 1 illustrates the operation of a conventional blood pressure measuring apparatus of the oscillometric type, of which there exists many varieties. For example, U.S. Pat. No. 4,263,918 of Swearingen et al discloses a blood pressure measuring apparatus utilizing a microcomputer, which apparatus varies the pressure in a cuff worn by a patient, generates a sequence of signals representing the amplitude of successive pressure pulses sensed in the cuff, and stores digital signals representing each pulse amplitude and the accompanying cuff pressure.

Figure 2:
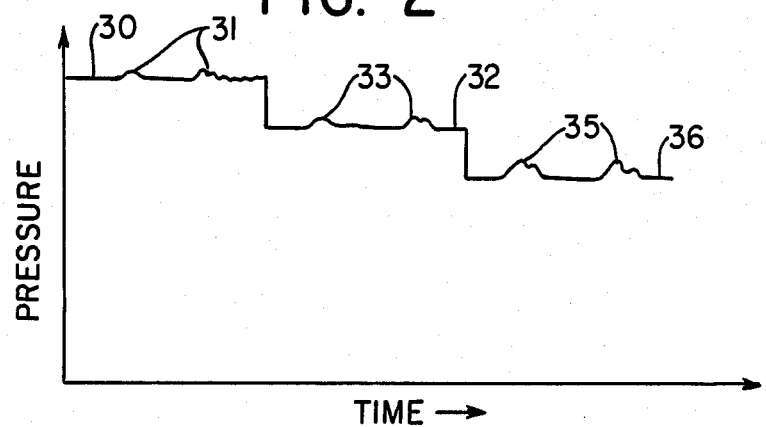
FIG. 2 is a wave form diagram illustrating the time varying pressure within the blood pressure cuff of FIG. 1, the wave form including a sequence of different pressure levels to which the cuff is inflated, as well as pulsatile perturbations resulting from the heartbeat of the patient.

An example of the operation of the portion of FIG. 1 described thus far will facilitate a better understanding of the invention. Typically, the operation of model acquisition logic 14 would result in cuff C being provided with a decreasing sequence of nominal pressures 32, 36 (see FIG. 2). At the same time, the patient's heartbeat produces pulsatile perturbations 31, 33, 35. FIG. 2 also represents the electrical signal produced by pressure transducer 16 and provided to pressure analyzer 18.

Figure 3:
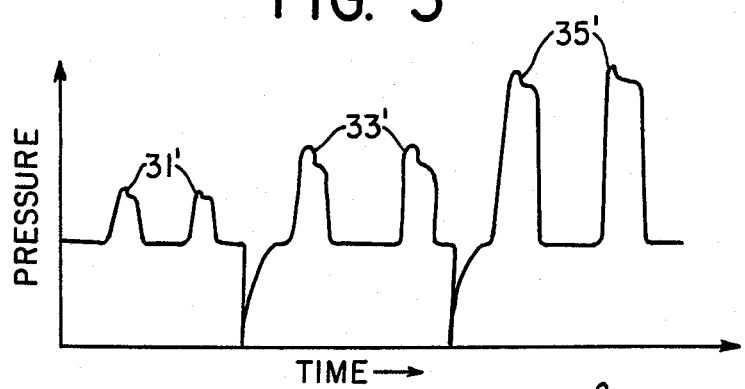
FIG. 3 is a wave form diagram illustrating the wave form of FIG. 2 after it has been processed to remove the variations in level and to emphasize the pulsatile perturbations.

In pressure analyzer 18, the pulsatile perturbations in FIG. 2 are stripped from the pressure wave form to produce a pulsatile wave form as exemplified by FIG. 3. This is, for example, achieved by bandpass filtering the signal of FIG. 2. A preferred form of bandpass filter would have a lower limit or "roll-off" frequency of about 0.25 Hertz and an upper roll-off frequency of about 30 Hertz. Once the pulses have been stripped from the stepped wave form of FIG. 2, they are readily amplified by conventional means, to produce the pulses 31', 33', 35' in FIG. 3.

Although the illustrative embodiment shows two pulses generated with respect to each pressure level applied to cuff C, it is possible to generate a greater or lesser number of pulses with respect to each level. A greater number of pulses would offer the benefit of providing more information for the estimation of an appropriate pulse height, thereby resulting in a better estimate. These estimates are generated in pressure analyzer 18, which, having generated a set of pulse heights and associated cuff pressures, provides information corresponding essentially to the curve of FIG. 4. In model acquisition logic 14, the successive pulse heights and accompanying cuff pressures are converted, by conventional means, to digital form and are then stored in memory 20.

Figure 4:
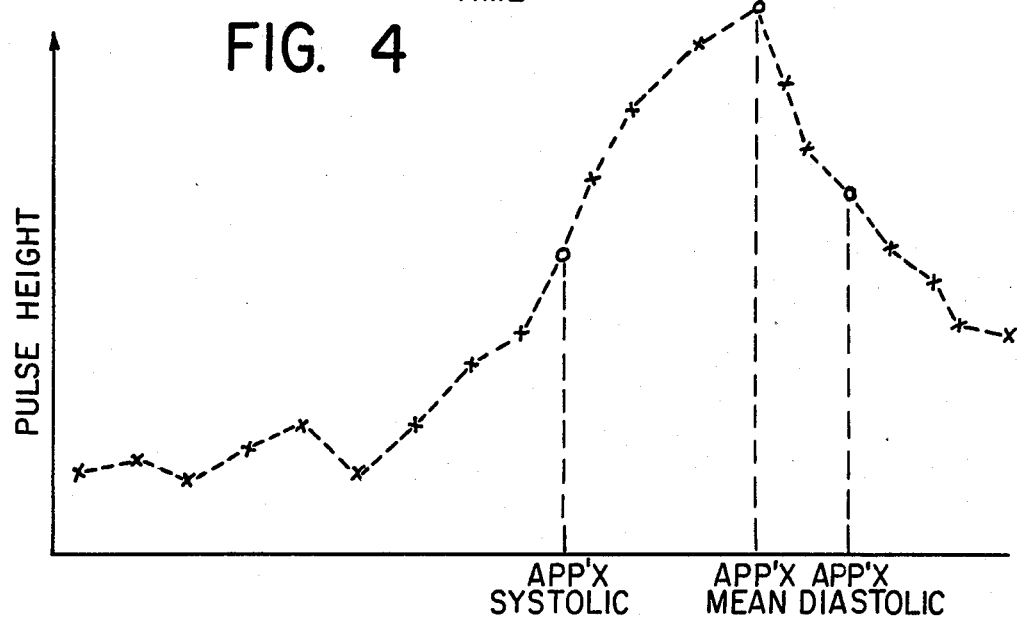
FIG. 4 illustrates a typical blood pressure model obtained with an oscillometric blood pressure measurement system.

FIG. 4 illustrates a typical, experimentally obtained blood pressure model for a patient. The "X" marks represent typical data points derived, for example, by pressure analyzer 18 of FIG. 1. The "O" marks represent the estimates of systolic, mean, and diastolic pressure, to be discussed further below.

It will be appreciated that the portion of FIG. 1 discussed so far will result in the acquisition of a blood pressure model for a patient and its retention in memory 20. An apparatus according to the invention would then be capable of a new, "quick update" mode of operation in which a predefined index characteristic, such as systolic pressure, is monitored, and changes are sensed rapidly, without having to derive a new model. This quick update mode of operation is accomplished by means of update logic 24 of FIG. 1, which replaces model acquisition logic 14 during the quick update mode. Update logic 14 therefore controls pump control 12, receives pulse and pressure information from pressure analyzer 18, communicates with memory 20, and updates display 22. When the quick update mode terminates, control reverts to model acquisition logic 14.

Following model acquisition, update logic 24 generates a characteristic curve which represents the blood pressure model in a region about the index characteristic (e.g. the systolic value). Making use of the characteristic curve and the pulse height and cuff pressure information received from pressure analyzer 18, update logic 24 produces an estimate of the pressure corresponding to the index characteristic.

Figure 5:
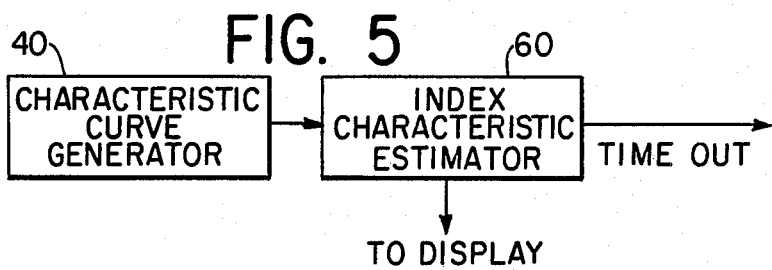
FIG. 5 is a functional block diagram illustrating the structure of update logic 24 in FIG. 1.

FIG. 5 is a functional block diagram illustrating the operation of update logic 24. Those skilled in the art will appreciate that the operations of update logic 24 could readily be incorporated in a program for a microprocessor. Alternatively, update logic 24 could be incorporated in the programming for a microcomputer in an existing blood pressure measuring apparatus. The quick update mode could be initiated automatically upon the acquisition of an acceptable blood pressure model, or through an operator actuated control.

Figure 6:
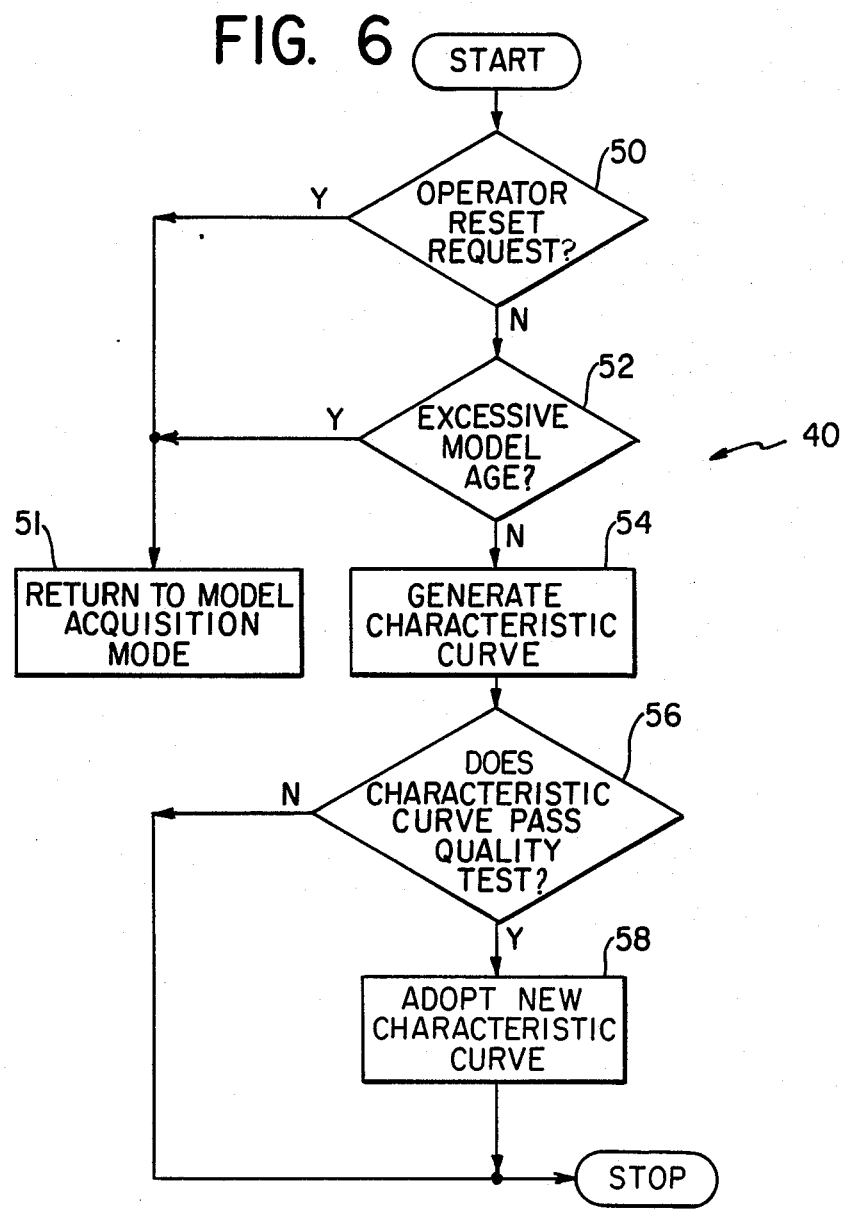
FIG. 6 is a flow chart demonstrating the operation of characteristic curve generator 40 of FIG. 5.

The block diagram of FIG. 6 illustrates the operation of characteristic curve generator 40. After the quick update mode is initiated, a test is performed in block 50 to determine whether the operator has requested a reset. Such a request would be likely only in an apparatus in which the quick update mode is entered automatically upon the acquisition of an acceptable model. If the operator has requested a reset, operation returns to the model acquisition mode (block 51).

Assuming that there has been no operator reset, a test is made at block 52 to determine whether the model is sufficiently current (i.e. whether "model age" is excessive). Such a test would, typically, be performed with the aid of a timer which is started when an acceptable model is obtained in model acquisition logic 14. A predetermined time after the acquisition of the model, the timer would be "timed out", an indication of excessive model age would be provided to the operator, and operation returns to the model acquisition mode at block 51.

Assuming that the operator has not requested a reset and model age is not excessive (in either case, operation would return to the acquisition mode), a characteristic curve is generated at block 54. The characteristic curve represents the blood pressure model in a region about the index characteristic, providing a continuous relationship between pulse height and accompanying pressure in that region. Making use of the characteristic curve, it is therefore possible to derive an estimate for the index characteristic on a continuous basis. This is accomplished by inflating the cuff to the nominal pressure corresponding to the index characteristic and monitoring pulse height. From the characteristic curve, every change in pulse height can be reflected as shift in the pressure corresponding to the index characteristic.

Without incurring unreasonable errors, it can safely be assumed that the blood pressure model represented in FIG. 4 will remain relatively stable. That is, the curve may shift laterally along the horizontal axis, but its shape will not change appreciably between updates of the model. By tracking an index characteristic, such as the systolic value, the device of the invention is, to a reasonable approximation, tracking short-term shifts of the entire blood pressure model.

In the preferred embodiment, the index characteristic is the systolic value, but tracking actually takes place at 5 mm Hg below the systolic value, in order to avoid entry into the relatively flat and unreliable region to the left of systolic in FIG. 4. The characteristic curve is that straight line which is obtained by providing a least-squares fit to those data points in the blood pressure model which lie between the systolic and mean values.

Following its generation, the characteristic curve is subjected to a quality test at block 56 and, if the curve passes the test, it is adopted as the new characteristic curve at block 58. If the newly generated characteristic curve does not pass the quality test, the previous characteristic curve is maintained, unless the blood pressure model is newly derived. In this latter case, failure to obtain an acceptable characteristic curve could require reentry to the acquisition mode to derive a new model.

In the preferred embodiment, the quality test is performed with the aid of a "smoothed" blood pressure model curve. The smoothed curve is obtained by replacing each data point in the blood pressure model with the average of itself, the immediately preceding data point, and the immediately following data point. The actual quality test involves determining and comparing the pressure which corresponds to the index point in the smoothed model and the characteristic curve, respectively. If the difference between these two values exceeds a predetermined amount, the new characteristic curve is rejected.

Upon the completion of the quality test, there will be a qualified characteristic curve in use, either the new one or the old one, and control is transferred to index value estimator 60. As will be explained below, index value estimator 60 actually performs the quick updating function by maintaining a constantly updated value of the pressure corresponding to the index characteristic. This value is utilized to update display 22 in FIG. 1. Index characteristic estimator 60 contains an internal timer, which causes operation to return to the model acquisition mode after a predetermined time, resulting in a "timeout."

Figure 7A:
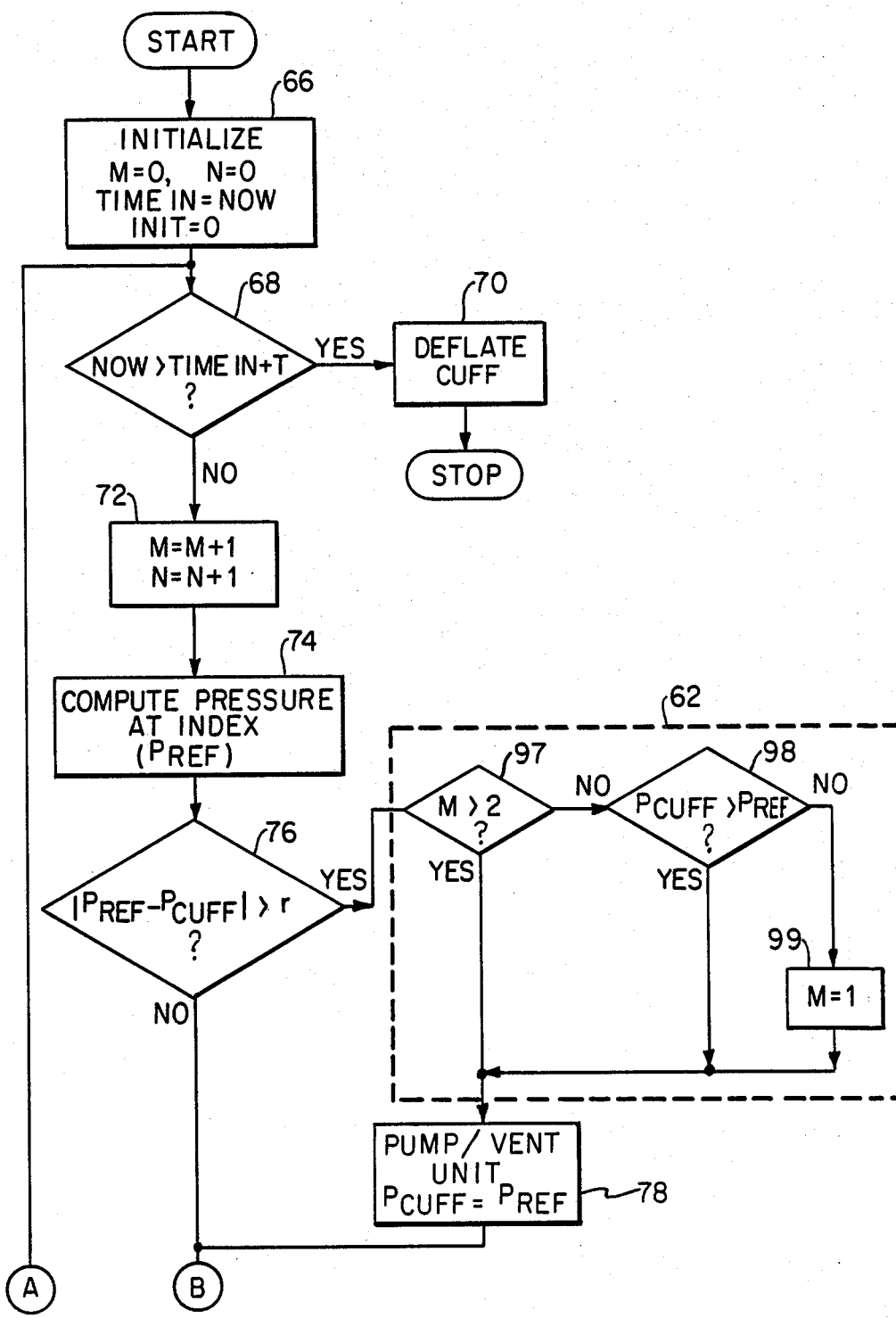

FIGS. 7A and 7B cooperatively define a block diagram illustrating the operation of index characteristic estimator 60. The portions of FIGS. 7A and 7B enclosed in dashed boxes 62 and 64 relate primarily to initialization of index characteristic estimator 60. Inasmuch as the remainders of FIGS. 7A and 7B are of a more general nature and relate to the steady-state operation of index characteristic estimator 60, those portions of the figures will be discussed first.

Variables utilized in index characteristic estimator 60 are initialized in block 66, after which estimator 60 enters an operational loop which is repeated constantly. During the first few passes through the loop, estimator 60 performs an initialization process in order to "lock on" to an acceptable estimate for the index value. The variables M, N and INIT relate to this initial start up of estimator 60 and will be discussed further below. The variable NOW stores the value of a real time clock. Upon initialization, a variable TIMEIN is set equal to NOW.

The main loop begins at block 68, where the real time clock NOW is tested to determine whether it exceeds TIMEIN by an amount greater than T. If this test produces a negative result, the main loop is traversed one more time. However, should this test produce a positive result, it would be indicative of the estimator 60 having been operative for an interval greater than T since its initialization. Under these circumstances, cuff C is completely deflated at block 70 and operation of estimator 60 stops. The operator would then have the option of manually restarting estimator 60, or taking some other action. The primary reason for this timeout is to permit blood circulation to return to normal and to avoid prolonged periods of constriction of the circulation.

Although the timeout has been illustrated as resulting in the termination of the operation of estimator 60, it is alternatively possible to have the timeout as only a temporary pause, after which the cuff is once more inflated, and normal operation resumes. This is illustrated by blocks 67, 69, 71, 73 and 75 in FIG. 7A, which are connected to the remainder of the block diagram by dashed lines, to symbolize that this is an alternative mode of operation of estimator 60. When operating in this mode, operation of estimator 60 is terminated only upon active intervention by the operator. A test for such intervention is made at block 67. In the absence of interruption of operation by the operator, a test is then performed at block 69 to determine if the model age is excessive. If so, operation returns to the model acquisition mode at block 71. If the model is not too old, operation of estimator pause at block 73 for a predetermined period of time. Thereafter, the cuff is re-inflated, at block 75, to its previous pressure, and operation of estimator 60 is once more initialized.

The index variables M and N are incremented at block 72, upon each passage through the loop. Then, at block 74, the pressure, $P_{REF}$, corresponding to the index characteristic is computed. In the preferred embodiment, the index characteristic is the systolic value, and this is estimated by tracking a point which is 5 mm Hg below systolic. At block 74, $P_{REF}$ would therefore be computed as 5 mm Hg below the most recent estimate of systolic pressure. Typically, this would be the systolic pressure estimated during the last transition through the main operating loop. However, when the quick update mode is first initiated, this would be the estimate of systolic derived by model acquisition logic 14.

At block 76, a test is performed to determine if cuff pressure is within a range, r, of $P_{REF}$. If not, cuff C is pumped or vented (block 78) to a pressure equal to $P_{REF}$. In the preferred embodiment, the cuff pressure is adjusted if it is not within plus or minus 5 mm Hg of $P_{REF}$. By maintaining $P_{CUFF}$ within a relatively close range of $P_{REF}$, it has been possible to use a linear approximation of the characteristic curve, with a substantial degree of accuracy.

At block 80, pulse height, H, is measured. This merely involves making use of the pulse height information provided by pressure analyzer 18. At block 82, this pulse height is used to estimate the index value from the characteristic curve. As has been mentioned previously, in the preferred embodiment the characteristic curve is a straight line. Specifically, the characteristic curve is defined by the following equation:

$$H = LSTSLP * (P_{CUFF} - P_{REF}) + LSTINT$$

where LSTSLP represents the last slope of the characteristic curve and LSTINT represents the last intercept of the characteristic curve with the line defined by the equation:

pressure = systolic − 5.

Defining TEMP as a temporary estimate of systolic, the linear characteristic curve would lead to the following equation for the derivation of TEMP:

$$TEMP = \frac{H - LSTINT}{LSTSLP} + P_{CUFF} + 5 \quad (1)$$

In the preferred embodiment (represented in FIG. 8), block 82 would therefore include a block 82-1 which realizes equation (1). In addition, it includes a block 82-2 which performs averaging. That is, the estimate for the systolic value, SYS, is obtained by taking the average between the previous value of SYS and TEMP. This averaging has a smoothing effect.

In Block 84, pulse rate is computed by a conventional technique. This could, for example, be accomplished by counting the number of clock pulses occurring between successive heart pulses, to measure the duration between heart pulses. Pulse rate is then computed in an obvious manner.

In Block 86 and 88 the values of the index variables N and M are tested, and the display is updated in block 90, only if M and N both exceed 2. If M or N fails to exceed 2, control returns to block 68, and the main operating loop is once again repeated.

In order to facilitate description of the stead-state loop operation in FIGS. 7A and 7B, description of the operation during the first few initializing passes through the loop has been deferred. As has been already explained, the preferred embodiment monitors the systolic value by tracking a value which is 5 mm Hg lower. When operation is initiated at block 66 of FIG. 7A, the index N and the variable INIT are initialized at 0. During the first pass through the loop, N is incremented to 1 at block 72, and the systolic value provided by model acquisition logic 14 is utilized in the computations at blocks 74 and 82. In the preferred embodiment, the computation at block 82-2 results in a new systolic estimate which is the average between the old one and the estimated value TEMP. The decision at block 86 then advances processing to block 92, where INIT is set equal to half of TEMP (since the initial value of INIT is zero). The decision at block 94 then results in a second pass through the operating loop.

During the second pass through the main loop, N is incremented to 2, and the systolic value computed during the previous pass through block 82 is utilized in the computations at blocks 74 and 82. In the preferred embodiment, the systolic value is computed, at block 82-2, as the average between the previous value and the newly computed value of TEMP. The test at block 86 results in a re-computation of INIT at block 92. The new value of INIT is equal to its previous value plus half the value of TEMP. Inasmuch as the previous value of INIT was half of TEMP, the newly computed value of INIT is the average of the last two TEMP estimates. The test at block 94 then results in the systolic value being set equal to INIT at block 96. After this second pass through the main operating loop, the systolic value is therefore equal to the average of the past two values of TEMP. Inasmuch as TEMP is the estimate from of the systolic value derived from the characteristic curve, the estimate of the systolic value derived during the second pass through the main loop is equal to the average between two successive estimates derived from the characteristic curve. This averaging is performed to achieve a smoothing or filtering effect. Those skilled in the art could implement this smoothing with many different types of digital filters without deviating from the scope or spirit of the invention.

This last estimate of the systolic value is utilized in the computations at blocks 74 and 82 during the next (third) pass through the main loop. During this pass, N is incremented to 3, so that the test at block 86 will be followed by the test at block 88, and this will be followed by either an update of the display or a further pass through the main loop, depending upon whether the index M is greater than 2 or not.

From the immediately preceding description, it will be appreciated that the index N is utilized to provide assurance that the display will not be updated until at least the third pass through the main loop. The reason for this operation is to assure that the system has a number of passes through the main loop to "lock-on" to a reliable estimate of the index value.

The index M is utilized to provide further assurance of a reliable index characteristic estimate in the preferred embodiment. From experience, it has been found that, when the cuff pressure is increased in order to set it equal to $P_{REF}$ (for example at block 78), an additional pass through the main loop is required, in order that the index value be based upon an additional estimate of TEMP. This operation is achieved within dashed box 62. Assuming that during the first two passes through the loop, $P_{CUFF}$ is found to be out of the range r of $P_{REF}$, the test at block 76 results in a test at block 97, which results in performance of the test at block 98. If $P_{CUFF}$ is not greater than $P_{REF}$ (i.e., if it will be necessary to increase the cuff pressure to inflate the cuff to $P_{REF}$), index M is set equal to 1 at block 99, and the cuff is subsequently pressurized at block 78. The subsequent test at block 88 will assure at least two additional passes through the main loop and the performance of at least three additional estimates at block 82 subsequent to the inflation of the cuff.

Although a preferred embodiment of the invention has been disclosed for illustrative purposes, those skilled in the art will appreciate that many additions, modifications, and substitutions may be made without departing from the scope and spirit of the invention as defined in the accompanying claims.

What is claimed is:

1. In an oscillometric blood pressure measuring apparatus of the type measuring pulsatile perturbations in a patient's blood pressure at a plurality of different measurement pressures of a sphygmomanometer cuff, to derive a blood pressure model for the patient, the model being stored in the apparatus as a series of pulsatile perturbations together with the associated cuff pressures, the improvement comprising:
   means operative on the stored model for generating a characteristic curve approximating the stored model in the vicinity of a predefined index value of cuff pressure;
   means for maintaining the pressure of said cuff within a predetermined range, r, of said index value; and
   means jointly responsive to said characteristic curve and to the magnitude of sensed pulsatile perturbations in said cuff pressure for tracking changes in said index value, to estimate a new value for said index value.

2. Apparatus in accordance with claim 1, wherein said generating means includes means for measuring the amount of time since the derivation of the blood pressure model and means for causing the derivation of a new model when said amount of time exceeds a predetermined value.

3. Apparatus in accordance with claim 1, wherein said generating means includes means for testing the accuracy of a newly generated characteristic curve, the newly generated curve being adopted as the characteristic curve only if it passes the accuracy test.

4. Apparatus in accordance with claim 3, wherein said means for testing includes means for producing a smoothed blood pressure model, and means jointly responsive to said smoothed blood pressure model and said characteristic curve for comparing the same and rejecting the characteristic curve when it differs from the smoothed blood pressure model to a predefined extent.

5. Apparatus in accordance with claim 4 wherein said means for producing a smoothed blood pressure model includes means for averaging each measured pulsatile perturbation of a blood pressure model with the perturbations stored immediately prior and subsequent thereto to derive said smoothed blood pressure model.

6. Apparatus in accordance with claim 1, wherein the index value is the systolic value and said generating means produces a curve which is a straight line providing a least-squares fit to those points in the blood pressure model which correspond to a cuff pressure between the systolic value and the means pressure.

7. Apparatus in accordance with claim 6, wherein said generating means generates said characteristic curve as a straight line defined by the following formula:

$$H = LSTSLP * (P_{CUFF} - P_{REF}) + LSTINT$$

where H is the height of the pulsatile perturbation, LSTSLP is the slope of the characteristic curve, $P_{CUFF}$ is the pressure of the cuff, $P_{REF}$ is the cuff pressure corresponding to the index value, and LSTINT is the intercept of the characteristic curve with the line defined by the equation:

$$pressure = systolic - 5.$$

8. Apparatus in accordance with claim 7, wherein said tracking means estimates the current pressure corresponding to the systolic value by means of a variable TEMP determined by the equation:

$$TEMP = \frac{H - LSTINT}{STSLP} + P_{CUFF} + 5.$$

9. Apparatus in accordance with claim 7, wherein said generating means includes means for testing the accuracy of a newly generated characteristic curve, the newly generated curve being adopted as the characteristic curve only if it passes the accuracy test, a prior characteristic curve being adopted otherwise, said means for testing including means for averaging each measured pulsatile perturbation of a blood pressure model with the perturbations stored immediately prior and subsequent thereto to derive a smoothed blood pressure model, and means jointly responsive to said smoothed blood pressure model and said characteristic curve for comparing the same and rejecting the characteristic curve when it differs from the smoothed blood pressure model to a predefined extent.

10. Apparatus in accordance with claim 1, wherein said maintaining means maintains said cuff pressure within a range, r, of a pressure which is 5 mmHg below the index value.

11. Apparatus in accordance with claim 10, wherein said range is plus or minus 5 mmHg.

12. Apparatus in accordance with claim 1, further comprising means for periodically deflating said cuff to substantially zero pressure.

13. Apparatus in accordance with claim 12, further comprising means for retaining said cuff in its deflated condition for a predetermined period of time, and means for thereafter restoring said cuff to its inflated condition.

14. Apparatus in accordance with claim 1, wherein said tracking means produces estimates of the index value by applying a value corresponding to the height of sensed pulsatile perturbations to the characteristic curve.

15. Apparatus in accordance with claim 14, wherein said tracking means produces a new estimate for the pressure corresponding to the systolic value by averaging the variable TEMP with at least one previous estimate therefor.

16. Apparatus in accordance with claim 15, further comprising means for displaying at least the pressure corresponding to the index characteristic value, first disabling means for disabling updating of said display means until at least two estimates of TEMP have been derived subsequent to deflation of said cuff in the process of maintaining the pressure thereof within said predetermined range.

17. Apparatus in accordance with claim 16, further comprising second disabling means for disabling updating of said display means until at least three estimates of TEMP have been derived subsequent to inflation of said cuff in the process of maintaining the pressure thereof within said predetermined range.

18. Apparatus in accordance with claim 15, further comprising means for displaying at least the pressure corresponding to the index characteristic value, and disabling means for disabling updating of said display means until at least three estimates of TEMP have been derived subsequent to inflation of said cuff in the process of maintaining the pressure thereof within said predetermined range.

19. A method for use in an oscillometric blood pressure measuring apparatus of the type measuring pulsatile perturbations in a patient's blood pressure at a plurality of different measurement pressures of a sphygmomanometer cuff, to derive a blood pressure model for the patient, the model being stored in the apparatus as a series of pulsatile perturbations and the associated cuff pressures, the method comprising the steps of:
generating a characteristic curve approximating the stored model in the vicinity of a predefined index value of cuff pressure;
maintaining the pressure of said cuff within a predetermined range, r, of said index value; and
tracking changes in said index value by sensing a pulsatile perturbation in said cuff pressure, deriving the corresponding value for cuff pressure from said characteristic curve, and utilizing the derived pressure as a new estimate for the index value.

20. The method of claim 19, wherein said generating step includes measuring the amount of time since the derivation of the blood pressure model and initiating the derivation of a new model when said amount of time exceeds a predetermined value.

21. The method of claim 19, wherein said generating step includes testing the accuracy of a newly generated characteristic curve, and adopting the newly generated curve as the characteristic curve only if it passes the accuracy test.

22. The method of claim 21, wherein said testing step includes producing a smoothed blood pressure model, and comparing said smoothed blood pressure model and said characteristic curve and rejecting the characteristic curve when it differs from the smoothed blood pressure model to a predefined extent.

23. The method of claim 22, wherein said step of producing a smoothed blood pressure model includes the steps of averaging each measured pulsatile perturbation of a blood pressure model with the perturbations immediately prior and subsequent thereto to derive said smoothed blood pressure model.

24. The method of claim 19, wherein the index value is the systolic value and said generating step produces a straight line providing a least-squares fit to those points in the blood pressure model which correspond to a cuff pressure between the systolic value and the mean pressure.

25. The method of claim 24, wherein said generating step utilizes the following formula for the characteristic curve:

$$H = LSTSLP * (P_{CUFF} - P_{REF}) + LSTINT$$

where H is the height of a pulsatile perturbation, LSTSLP is the slope of the characteristic curve, $P_{CUFF}$ is the pressure of the cuff, $P_{REF}$ is the cuff pressure corresponding to the index value, and LSTINT is the intercept of the characteristic curve with the line defined by the equation:

$$pressure = systolic - 5.$$

26. The method of claim 25, wherein said tracking step comprises estimating the current pressure corresponding to the systolic value by means of a variable TEMP determined by the equation:

$$TEMP = \frac{H - LSTINT}{LSTSLP} + P_{CUFF} + 5.$$

27. The method of claim 26, wherein said tracking step comprises producing a new estimate for the pressure corresponding to the systolic value by averaging the variable TEMP with at least one previous estimate therefor.

28. The method of claim 19, wherein said generating step includes testing the accuracy of a newly generated characteristic curve, and adopting the newly generated curve as the characteristic curve only if it passes the accuracy test, a prior characteristic curve being adopted otherwise, said testing step including averaging each measured pulsatile perturbation of a blood pressure model with the perturbations immediately prior and subsequent thereto to derive a smoothed blood pressure model, comparing said smoothed blood pressure model and said characteristic curve and rejecting the characteristic curve when it differs from the smoothed blood pressure model to a predefined extent.

29. The method of claim 19, wherein said cuff pressure is maintained within a range, r, of a pressure which is 5 mmHg below the index value.

30. The method of claim 29, wherein said range is plus or minus 5 mmHg.

31. The method of claim 19, further comprising periodically deflating said cuff to substantially zero pressure.

32. The method of claim 31, further comprising retaining said cuff in its deflated condition for a predetermined period of time, and thereafter restoring said cuff to its inflated condition.

33. The method of claim 19, wherein said tracking step comprises applying a value corresponding to the height of sensed pulsatile perturbations to the characteristic curve and deriving therefrom a new estimate for the index value.

34. The method of claim 19, performed in an apparatus including means for displaying at least the pressure corresponding to the index value, said method further comprising the step of disabling updating of said display means until at least two estimates of TEMP have been derived subsequent to deflation of said cuff in the process of maintaining the pressure thereof within said predetermined range.

35. The method of claim 34, further comprising disabling updating of said display means until at least three estimates of TEMP have been derived subsequent to inflation of said cuff in the process of maintaining the pressure thereof within said predetermined range.

36. The method of claim 19, performed in an apparatus including means for displaying at least the pressure corresponding to the index value, said method further comprising the step of disabling updating of said display means until at least three estimates of TEMP have been derived subsequent to inflation of said cuff in the process of maintaining the pressure thereof within said predetermined range.

* * * * *